United States Patent [19]

Forbes Jones et al.

[11] Patent Number: 5,066,225
[45] Date of Patent: * Nov. 19, 1991

[54] CRYSTALLINE ALUMINA ORTHODONTIC BRACKET

[75] Inventors: Robin M. Forbes Jones, Pennington; Carl Panzera, Bellemead; Robert D. DeLuca, Pennington, all of N.J.

[73] Assignee: Johnson & Johnson Consumer Products, Inc., Skillman, N.J.

[*] Notice: The portion of the term of this patent subsequent to Jan. 27, 2004 has been disclaimed.

[21] Appl. No.: 932,745

[22] Filed: Nov. 19, 1986

Related U.S. Application Data

[63] Continuation-in-part of Ser. No. 743,851, Jun. 12, 1985, Pat. No. 4,639,218, which is a continuation-in-part of Ser. No. 602,876, Apr. 23, 1984, abandoned, and Ser. No. 707,281, Mar. 6, 1985, abandoned.

[51] Int. Cl.[5] .................................................. A61C 7/00
[52] U.S. Cl. .................................................... 433/8
[58] Field of Search ..................... 433/201.1, 8, 9, 10, 433/11, 12, 13, 14

[56] References Cited

U.S. PATENT DOCUMENTS

| | | | |
|---|---|---|---|
| 4,122,605 | 10/1978 | Hirabayashi et al. | 433/201.1 |
| 4,219,617 | 8/1980 | Wallshein | 433/8 |
| 4,639,218 | 1/1987 | Jones et al. | 433/8 |

Primary Examiner—Cary E. O'Connor

[57] ABSTRACT

An orthodontic bracket is made from crystalline alumina, preferably crystalline alpha-alumina. The bracket comprises a base member for attaching to a tooth and a body member extending from the base member. The body member includes walls that define an archwire groove. The walls comprise crystalline alumina. The bracket has sufficient strength to withstand normal torquing forces imparted by an archwire.

7 Claims, 11 Drawing Sheets

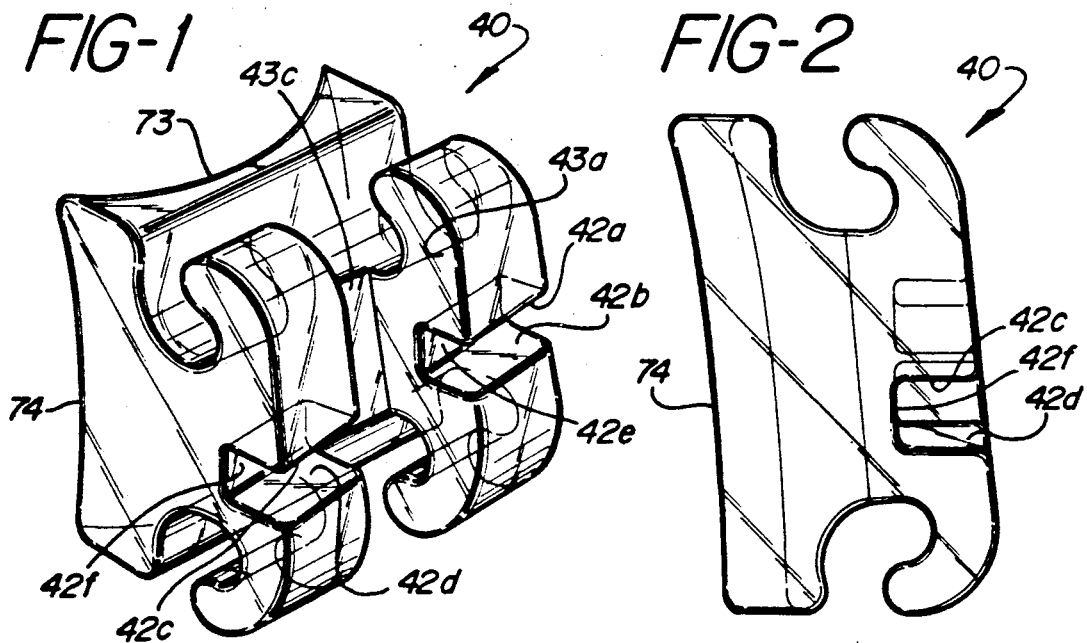

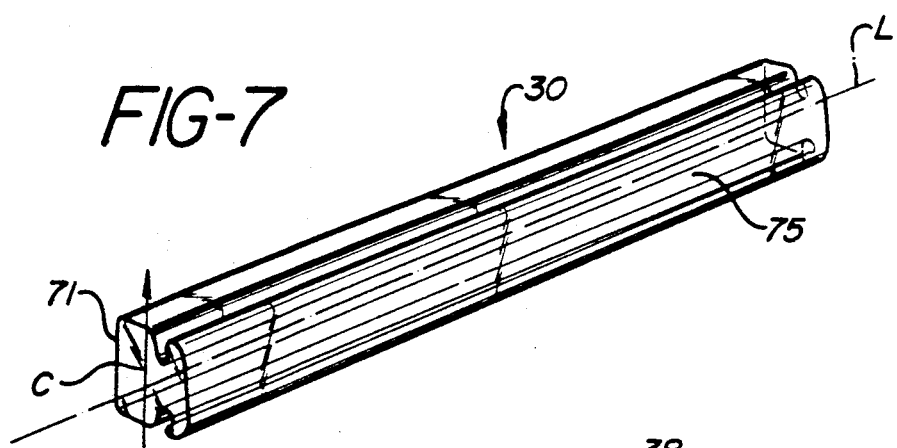
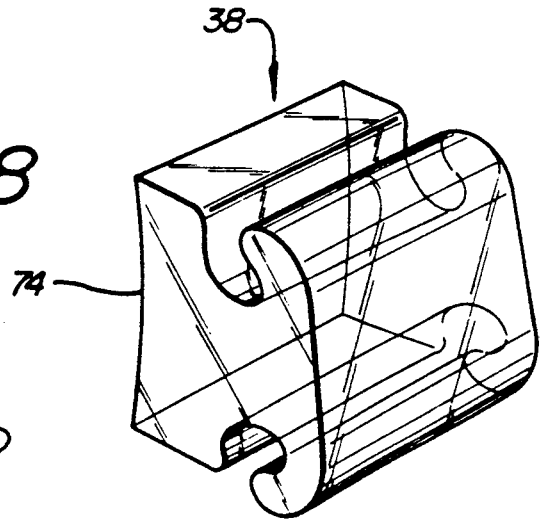
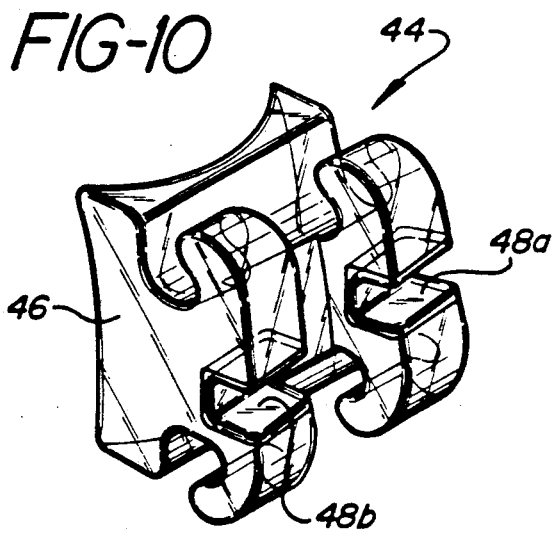
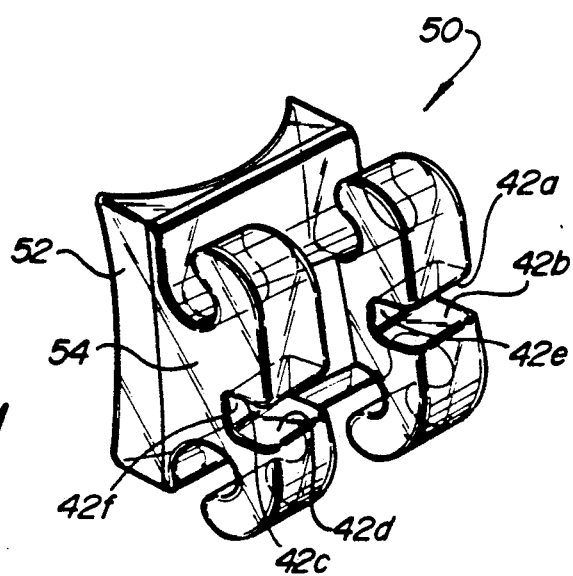

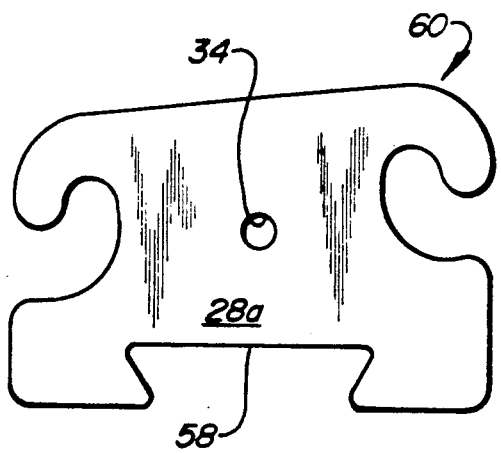
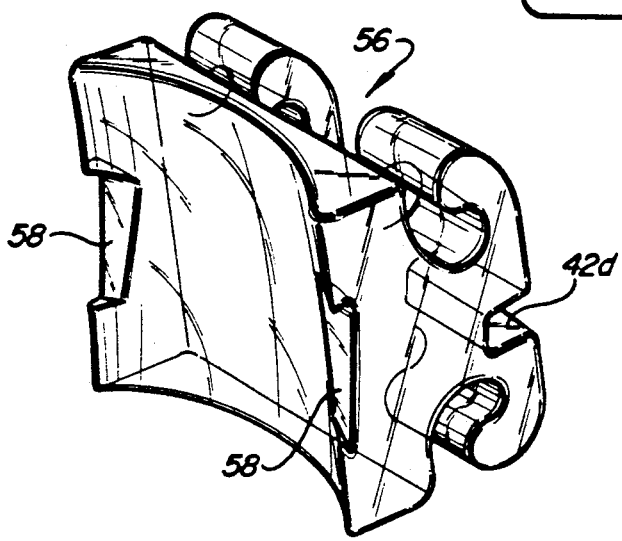
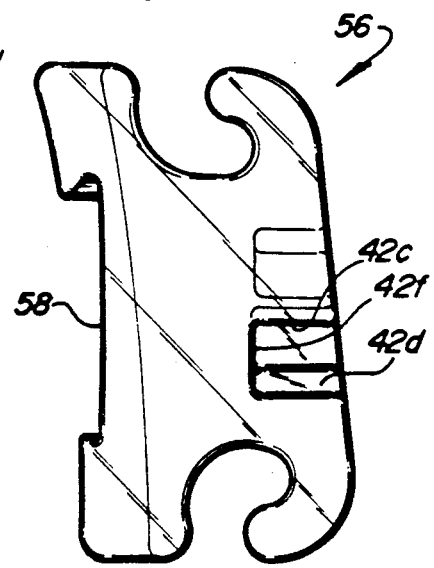
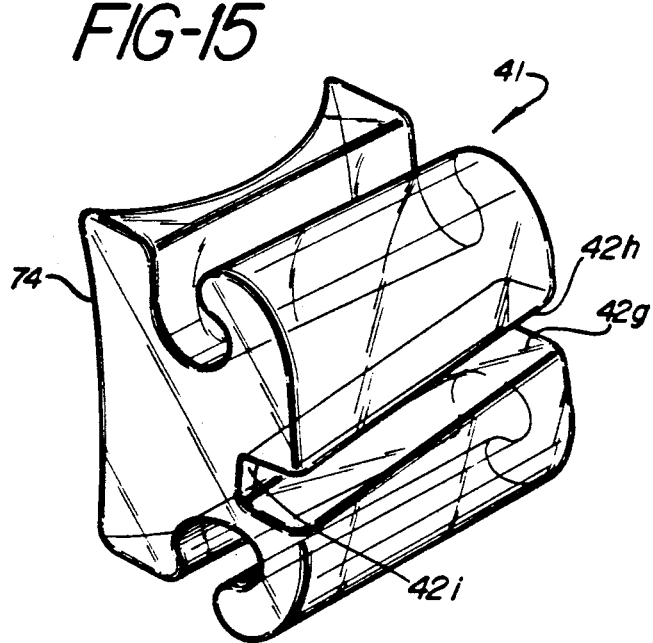

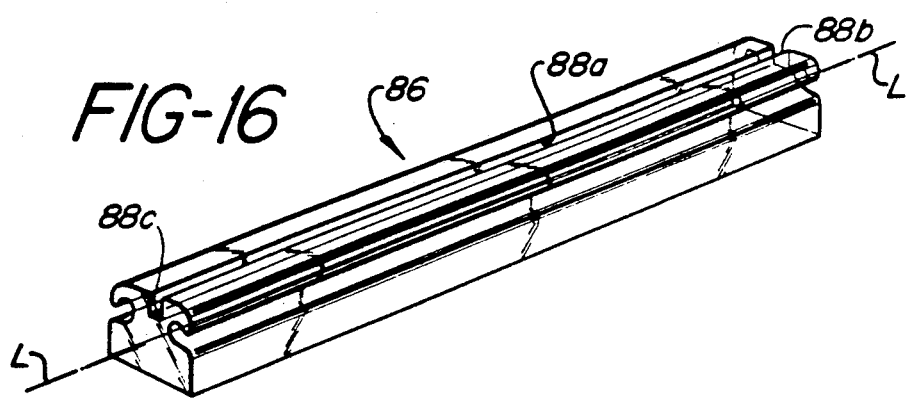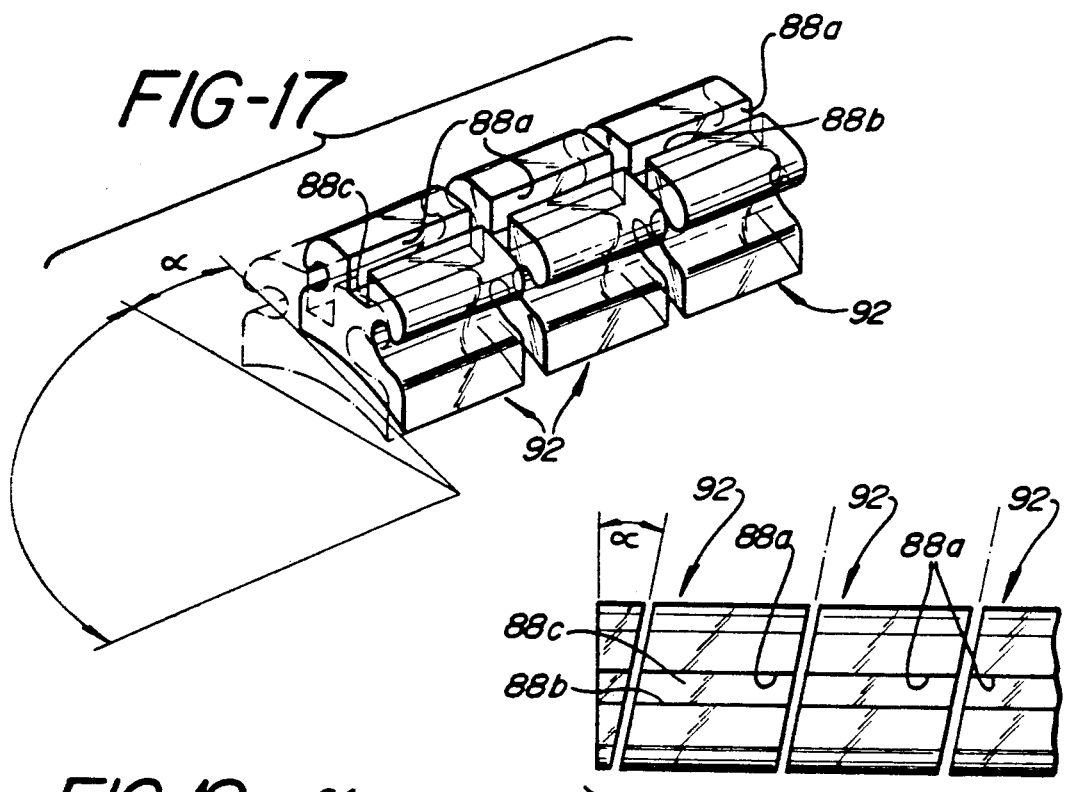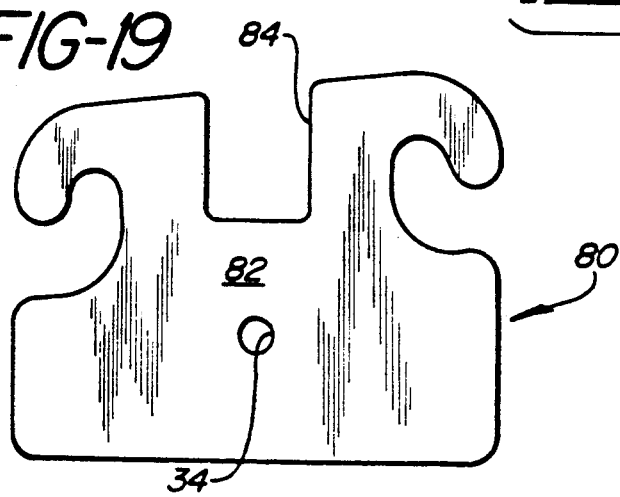

CRYSTALLINE ALUMINA ORTHODONTIC BRACKET

This application is a continuation-in-part of our copending application Ser. No. 743,851, filed June 12, 1985, now U.S. Pat. No. 4,639,218 was of our applications Serial No. 602,876, filed Apr. 23, 1984, and Ser. No. 707,281, filed Mar. 6, 1985. The latter two applications are now abandoned.

The invention relates to an orthodontic bracket comprising as a load bearing member a crystalline alumina material such as crystalline alpha-alumina.

BACKGROUND OF THE INVENTION

Orthodontic brackets attach directly to teeth and serve to transmit corrective forces from an orthodontic archwire to the tooth to which the bracket is attached. The requirements for an orthodontic bracket are quite severe. First, it must have sufficient mechanical strength to withstand the forces to which it will be subjected, including the forces transmitted by an archwire, ligation forces, and mastication forces. Second, it must be chemically inert in the oral environment so that it will not corrode and will be and remain biologically inert. The bracket must meet these requirements, and still remain small enough to fit on the tooth. Despite proposals for making orthodontic brackets from many different materials the overwhelming majority of orthodontic brackets in use today are made of metal, usually stainless steel. Metal brackets meet all of the essential requirements, but they have one undesirable attribute—they are unsightly. A person undergoing orthodontic treatment has a conspicuous amount of metal in full view on the front surfaces of his or her teeth. And since the treatment normally extends over a number of years, this unsightly appearance must be endured for a considerable period of time.

The incentive to make brackets from less unsightly materials has existed for many years. But recently, orthodontic treatment has been given to increasing numbers of adults for whom the unsightly appearance of metal brackets is more than a mere annoyance. Therefore, the incentive to provide more esthetic orthodontic treatment is even greater now than it has ever been.

To avoid the unsightly appearance of metal orthodontic brackets, it is now possible in some (but not all) cases to install the brackets and archwire on the lingual (tongue) side of the teeth. However, the lingual side technique usually takes much longer than the customary buccal side technique to complete the treatment. Also the brackets and archwire sometimes interfere with the tongue during speech. It has been proposed to make orthodontic brackets out of less unsightly material, such as transparent or translucent plastic (e.g , polycarbonate), or ceramic materials which more closely resemble natural dentition. A problem with both plastic materials and ceramics is that their mechanical strengths are borderline, and bracket breakage can be a signlficant problem with them. The ceramic brackets that are currently in use are rather bulky (to overcome the physical property limitations of the material), so they tend to be somewhat uncomfortable to the patient. From an esthetic viewpoint, neither plastic nor ceramic are fully satisfactory either, because plastic may discolor (from coffee or tobacco, for example), and the color of ceramic rarely matches natural dentition. In an effort to overcome the strength limitations of ceramic and plastic brackets, it has been proposed to reinforce such brackets with metal inserts or metal liners (for the archwire groove). While this may help (although it will not fully alleviate) the strength limitations of plastic or ceramic brackets, such solutions bring back, to at least a limited degree, the esthetic problem for which the plastic or ceramic bracket was the proposed solution. Thus, to date, there is no really satisfactory solution to the problem of unsightly metal orthodontic brackets.

BRIEF SUMMARY OF THE INVENTION

The invention provides a orthodontic bracket comprising a base member for attaching to a tooth and a body member extending from the base member. The body member includes walls that define an archwire groove, wherein said walls comprise a crystalline alumina material such as crystalline alpha-alumina. The strength and transparency properties of crystalline alpha-alumina and certain other crystalline alumina materials permit the provision of orthodontic brackets that are much more esthetic than metal brackets, but which alleviate to a large degree the strength limitations of plastic and ceramic brackets.

THE PRIOR ART

High alumina content, injection molded randomly oriented polycrystalline ceramic orthodontic brackets are disclosed by Reynolds in U.S. Pat. Nos. 4,216,583 and 4,322,206, and by Wallshein in U.S. Pat. No. 4,219,617. In order to enhance adhesion to the tooth, Reynolds mentions the possibility of providing an undercut portion in an aperture in the tooth contacting surface of his bracket. However such undercut portion would have to be machined, at prohibitive expense, since it is impossible to mold it. The commercial version of the Reynolds bracket lacks the undercut portion.

Plastic orthodontic brackets containing metal reinforcement and/or metal liners for the archwire groove are disclosed by Andrews in U.S. Pat. No. 3,930,311, Stahl in U.S. Pat. No. 3,964,165, Kurz in U.S. Pat. No. 4,107,844, Frantz in U.S. Pat. No. 4,299,569, and Wallshein in U.S. Pat. No. 4,302,532.

Hirabayashi et al., in U.S. Pat. No. 4,122,605, disclose a somatic element made of single crystalline sapphire. Specific elements disclosed include a screw type implant pin, a blade type implant pin, a pin type implant pin, and a compression plate Richardson, in U.S. Pat. No. 2,045 025, discloses a method for making orthodontic band brackets (i.e., the brackets that are attached to tooth engaging bands) wherein a longitudinal slot is cut in a bar of metal to form a bar that has a desired cross-sectional configuration, followed by cutting blanks from the bar and then machining the blanks to form the brackets.

The semi-conductor art has disclosed articles made of single crystal alumina having a coating of silica. For instance, see McKinnon et al., U.S. Pat. No. 3,764,507.

Hurley in U.S. Pat. No. 3,625,740, discloses a process for treating crystalline alpha-alumina surface with a silane to enhance adhesion to an epoxy resin. Daisley et al., in U.S. Pat. No. 4,415,330, disclose an orthodontic bracket in which the tie wings have a generally rhomboidal configuration.

BRIEF DESCRIPTION OF THE DRAWINGS

FIG. 1 is a perspective view of an orthodontic bracket made of crystalline alpha-alumina;

FIG. 2 is a side view of the bracket of FIG. 1;

FIG. 3 is a front view of the bracket of FIG. 1;

FIG. 4 is a top view of the bracket of FIG. 1;

FIG. 7 is a perspective view of a crystalline alpha-alumina rod produced by the apparatus of FIG. 6;

FIG. 8 is a perspective view of a bracket blank cut from the crystalline alpha-alumina rod of FIG. 7;

FIG. 10 is a perspective view of a plastic orthodontic bracket having a crystalline alpha-alumina liner in the archwire groove;

FIG. 11 is a perspective view of an orthodontic bracket having a plastic base, with the remainder of the bracket being crystalline alpha-alumina;

FIG. 12 is a view similar to FIG. 5, showing an alternative configuration of the top of the die;

FIG. 13 is a perspective view of a crystalline alpha-alumina orthodontic bracket having a keyway in the base for the purpose of enhancing the bonding of the bracket to the tooth;

FIG. 14 is a side view of the orthodontic bracket of FIG. 13;

FIG. 15 is a perspective view of a "single-wing" orthodontic bracket made of crystalline alpha-alumina;

FIG. 16 is a perspective view of an alternate crystalline alpha-alumina rod that can be produced by the apparatus of FIG. 6;

FIG. 17 is a perspective view of a series of bracket blanks as they are cut from the rod of FIG. 16;

FIG. 18 is a top plan view of the blanks of FIG. 17;

FIG. 19 is a top view of a die that is used to produce the rod of FIG. 16;

DETAILED DESCRIPTION OF THE INVENTION

This invention is directed to the provision of orthodontic brackets comprising as a load bearing member certain crystalline alumina materials, preferably crystalline alpha-alumina. As used herein, the term "crystalline alumina" is intended to include only essentially monocrystalline alumina, that is, alumina comprised of a single crystal or two or more single crystals grown together longitudinally but separated by a relatively small angle (usually within 4° determined with respect to the C-axes of neighboring single crystals) grain boundary.

In a preferred aspect of the invention, the orthodontic bracket is entirely crystalline alpha-alumina. Such a bracket can be produced by first drawing a crystalline alpha-alumina rod from a melt, wherein the rod has a predetermined cross-sectional configuration, by slicing the rod into individual blanks, and then machining the blanks to produce the bracket. As will be made apparent by the discussion below the cross-sectional configuration of the rod is approximately the configuration of the cross-section of an orthodontic bracket taken in a plane that is perpendicular to the top and bottom faces of the bracket and is approximately parallel to the two side faces of the bracket. (By "approximately parallel" is meant not more than about 12° from parallel, for reasons that will be made clear below.) The terms "top and bottom faces" and "side faces" refer to the top, bottom, and side surfaces, respectively, of the bracket when looking directly at the front of the bracket (the "front of the bracket" is the surface opposite the tooth contacting surface) in the position the bracket would assume when installed on a tooth with the patient in the upright position. In the embodiments illustrated herein, the brackets have one or, preferably, two pairs of tie wings, and the said plane is taken through a pair of tie wings. Thus, the said predetermined cross-sectional configuration will include, at a minimum, a pair of tie wings and a base.

The preferred procedure for producing a crystalline alpha-alumina rod having a predetermined cross-sectional configuration is the EFG (for Edge-defined, Film-fed, Growth) modification of the Czochralski process for growing crystalline alpha-alumina. The EFG process is described by LaBelle in "EFG - The Invention and Application to Sapphire Growth", in Journal of Crystal Growth, 50, pages 8–17 (September 1980). See also LaBelle, U.S. Pat. Nos. 3,591,348, and 3,870,477, LaBelle et al., U.S. Pat. Nos. 3,701,636 and 3,915,662 and other patents and articles cited in the Journal of Crystal Growth article.

Figure 6:
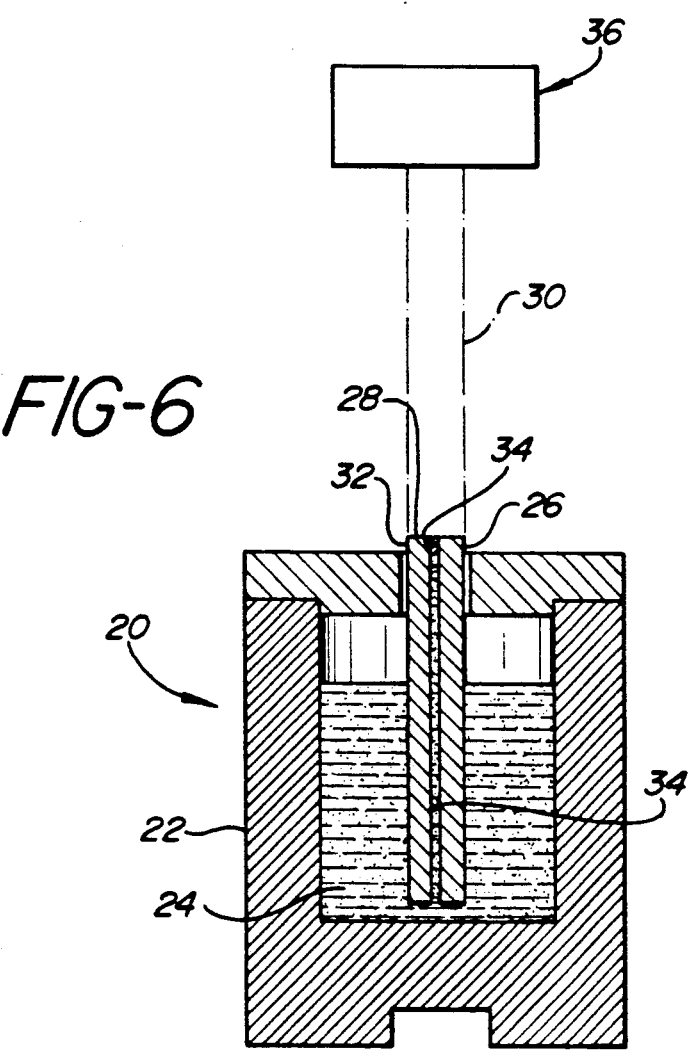
FIG. 6 is a schematic representation of apparatus for producing a crystalline alpha-alumina rod.

FIG. 6 is a schematic representation of apparatus for producing a crystalline alpha-alumina rod having a predetermined cross-sectional configuration by the EFG process. The apparatus 20 includes a crucible 22 containing molten alumina 24. A die 26 made of a suitable material such as molybdenum or iridium is positioned such that the bottom of the die 26 is immersed in the molten alumina 24, and the top of the die 26 is above the surface of the melt 24. A vertical distance from the top of the melt 24 to the top surface 28 of the die 26 of up to 50 millimeters is permissible. (This distance is exaggerated in FIG. 6 for clarity.)

Figure 5:
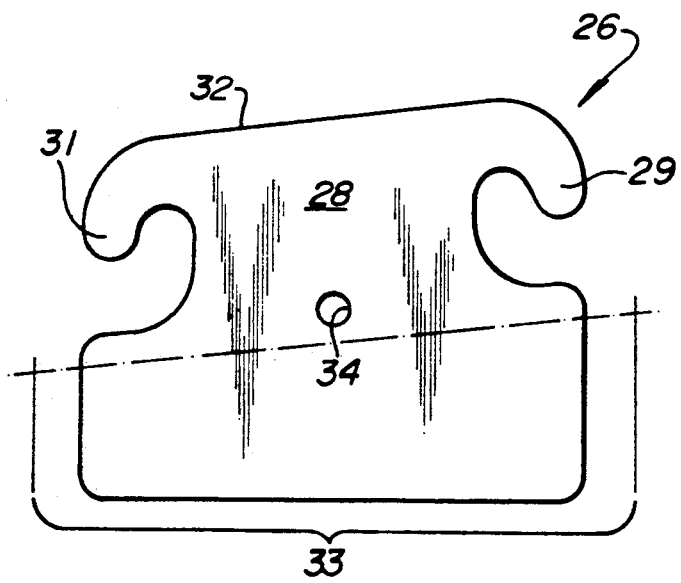
FIG. 5 is a top view of a die that is used to produce a crystalline alpha-alumina rod having a cross-sectional configuration essentially identical to the configuration of the top of said die.

FIG. 5 shows the top surface 28 of the die 26. The top surface 28 is smooth, flat, and has the overall approximate shape of the desired configuration of the cross-section of the crystalline alpha-alumina rod 30 (shown in FIG. 7) from which the brackets are made, including the configuration of a pair of tie wings shown as 29 and 31, and the base of the bracket, shown as 33. It is important that the sides 32 and the top surface 28 of the die 26 meet in a sharp 90° angle, in order to minimize imperfections in the surface of the growing rod 30. The die 26 contains a capillary passage 34 through which molten alumina 24 is drawn. The melt 24 is drawn from the crucible 22 through the capillary 34 to the top surface 28 of the die 26, where it spreads out and completely covers the said top surface 28 with a film of molten alumina. However, because molten alumina and molybdenum or iridium have the appropriate wettability relationship, the molten alumina film stops at the edge of the surface 28. Therefore, crystalline alpha-alumina crystal grown or pulled from this film of molten alumina assumes a cross-sectional configuration substantially exactly the same as the configuration of the top surface 28 of the die 26. Thus, the rod 30 (which had been started by a seed crystal, as in the Czochralski process) pulled by a pulling mechanism 36 from the film of molten alumina on the top surface 28 of the die 26 will have a cross-sectional configuration substantially identical to the configuration of the top surface 28 of the die 26. It has been found to be convenient to grow the rod 30 to a length of about two inches (about 5 centimeters) in order to minimize any machining problems that could be caused by the failure of the rod to grow exactly straight.

The crystal orientation of the growing rod may prove to be important (at least economically, and perhaps also from a performance standpoint) in the practice of the invention. In the case of crystalline alpha-alumina, the crystal orientation can be defined with reference to the C axis of the crystal. (The C axis is perpendicular to the plane which contains the simplest arrangement of atoms in the crystal unit cell. Stated another way the C axis is perpendicular to the plane which contains the $a_1$ and $a_2$ axes.) The minimum amount of strain developed in the growing crystal will occur if the C axis is found in a plane perpendicular to the longitudinal axis L of the rod 30. (See FIG. 7.) This has proven to be the optimum crystal orientation in some cases. (As is known in the art, the growing crystal will assume the crystal orientation of the seed crystal.) Regardless of the crystal orientation of the rod 30, it is preferred to anneal the rod 30 prior to machining so as to relieve stresses in the crystal to minimize the chances of breakage during machining. A typical annealing cycle would be to heat the rod 30 from room temperature up to 1950-2000° C. at an even rate for about two hours, to maintain the rod 30 at 1950°-2000° C. for 4 to 6 hours and to then cool the rod 30 down to room temperature at an even rate for two hours. The entire annealing cycle is preferably carried out under an inert atmosphere such as argon.

The crystalline alpha-alumina rod 30 is cut into individual blanks 38 (FIG. 8). each of which is machined into a bracket. FIGS. 1–4 are various views of an orthodontic bracket 40 made completely of crystalline alpha-alumina. The bracket 40 is made from the blank 38 by a series of cutting, grinding, and polishing steps, using known techniques for machining crystalline alpha-alumina. A diamond cutting wheel may be used to cut out the archwire groove defined by walls 42a, 42b, 42c 42d, 42e, 42f and the "saddle" defined by walls 43a, 43b, 43c of a double wing or twin bracket (such as shown in FIG. 1). A single wing bracket 41 is shown in FIG. 15. In the single wing bracket 41, the archwire groove is defined by walls 42g, 42h, 42i. Edges may be beveled by grinding, and corners rounded off by polishing, A convenient procedure for fabricating the bracket from the crystalline alpha-alumina rod 30 is the following:

The rod 30 is fastened to a rod holding fixture (not shown) with the base surface 71 facing out. The base surface 71 is then ground to an arcuate concavity with a diamond grinding wheel. The resulting concave surface is shown as 74 in FIGS. 1, 2, and 8. After the base has been ground to produce the concave surface 74. the rod may be reversed in the fixture and the top surface 75 may be ground to compensate for any dimensional differences arising from the crystal growing process. This ensures a precisely controlled base to top dimension.

The rod, with the base and top ground, may then be cut into blanks 38 (FIG. 8) with a diamond saw (not shown) by making cuts in a plane perpendicular to the longitudinal axis L of the rod 30.

The archwire groove and the saddle are then ground with a diamond grinding wheel. It is preferred to grind the archwire groove in two passes. For instance if the desired archwire groove is 20 mils wide and 30 mils deep the first pass will typically remove enough material to make a groove 15 mils wide and 20 mils deep. Following this procedure helps to minimize imperfections in the finished bracket A second arcuate concavity is then ground in the base or tooth contacting surface using a diamond grinding wheel. The thus ground concave surface is shown as 73 in FIGS. 1 and 4. The concave surfaces 73 and 74 are employed so that the contour of the base more nearly matches the surface contours of a tooth.

In an alternative embodiment of the invention, the archwire groove may be "grown" into the rod. This aspect is illustrated in FIGS. 16–21. By using a die 80 (FIG. 19) whose top surface 82 has a slot 84, a rod 86 can be grown having a longitudinal groove defined by walls 88a, 88b, 88c in it so that, when the individual brackets are cut from the rod 86 the brackets will already contain the archwire groove, as defined by the walls 88a, 88b, and 88c. By so doing, one step (i.e., the grinding of the archwire groove) in the procedure for producing the bracket can be eliminated, at a significant cost saving.

Because the dimensions of the cross-section of the archwire groove are quite small (e.g., 20 by 30 mils), it may be difficult to grow the archwire groove in the rod because the surface tension of the molten alumina may tend to close up the groove. Therefore, the archwire groove may also be ground in the rod to produce the grooved rod shown in FIG. 16. This is also a cost saving procedure because it is easier to handle the whole rod in the grinding operation than the individual blanks cut from the rod. It is probable that even where the groove is grown in the rod some grinding will be necessary to finish the groove to the desired dimensions.

One difference in the procedure for making the brackets in accordance with this alternative embodiment of the invention, whether the archwire groove is grown in the rod or ground in it is that the bracket blanks 92 that are cut from the rod 86 are cut at a slight angle. Thus, instead of making the cuts in the rod 86 in a plane normal or perpendicular to the longitudinal axis L of the rod, the cuts are made in the following manner:

Holding the rod 86 in position with the longitudinal axis L in a horizontal plane and the face having the longitudinal groove on top, each cut is made in a vertical plane that is angled slightly (e.g., up to about 12°) at an angle a from the vertical plane that is perpendicular to the longitudinal axis L of the rod 86. This is best seen in FIG. 18

Figure 24:
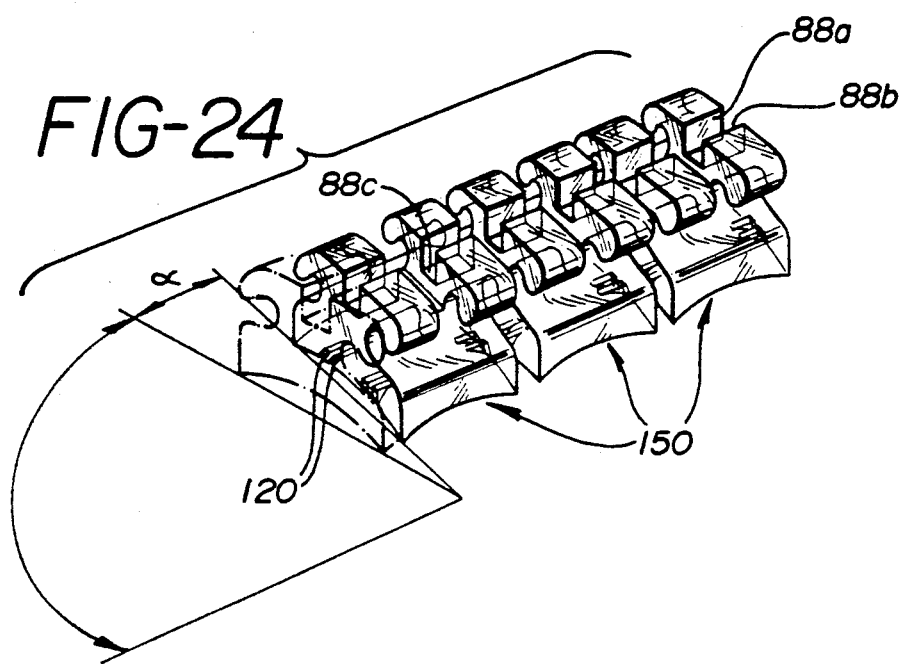
FIG. 24 is a perspective view of a series of brackets as they are cut from the rod of FIG. 23 showing also the saddles machined in the brackets.
Figure 25:
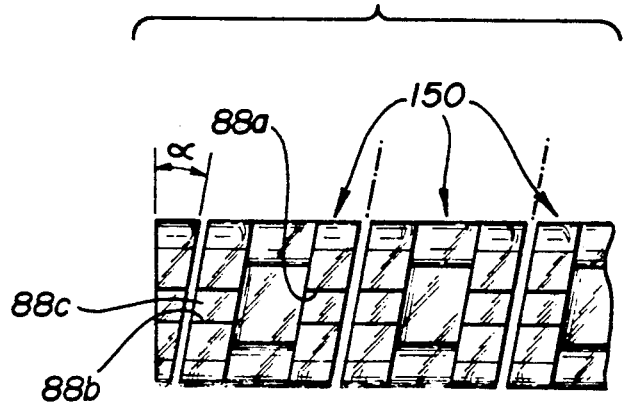
FIG. 25 is a top plan view of the brackets of FIG. 24.
Figure 26:
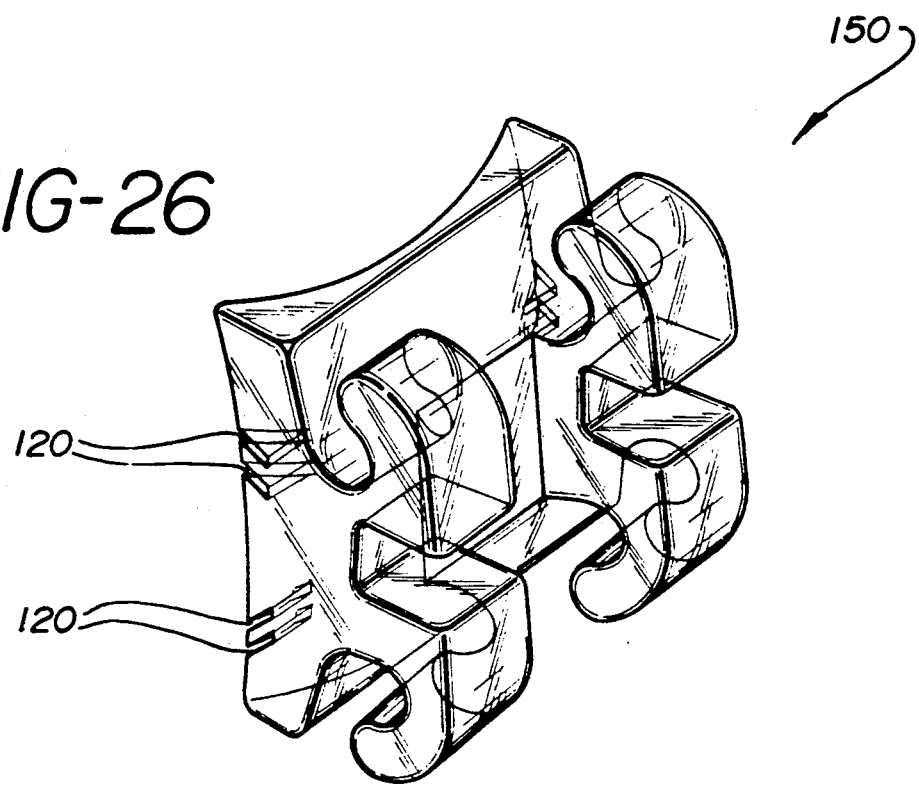
FIG. 26 is a perspective view of one of the brackets of FIGS. 24 and 25.
Figure 27:
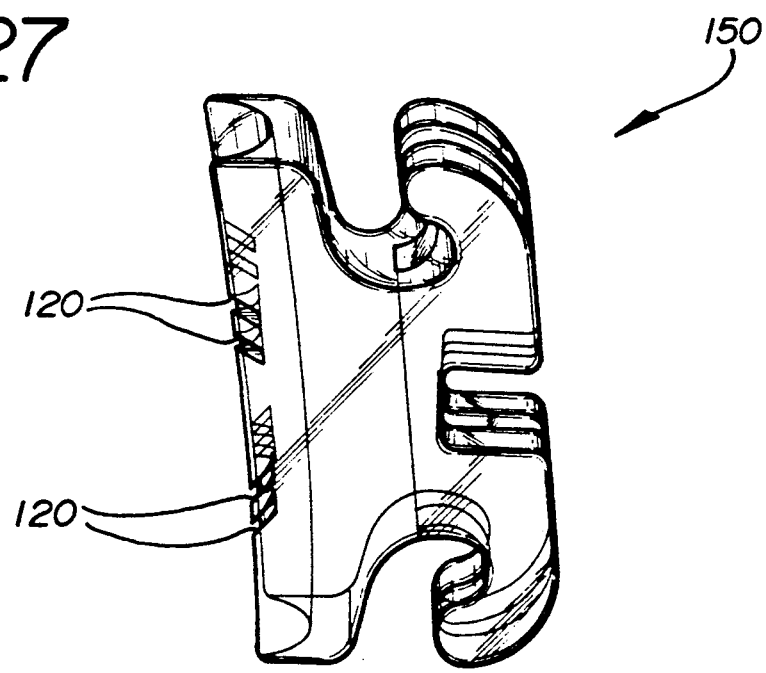
FIG. 27 is a side view of the bracket of FIG. 26.

The saddles and the second base concavities 73 can be machined in the bracket prior to cutting the individual brackets from the rod 86. This is preferred because it is easier to handle the rod 86 than the individual bracket blanks 92. The machining of the saddles can then be done with a diamond grinding wheel by feeding the rod stepwise to the wheel and cutting a series of grooves across the rod, wherein the said grooves will be oriented generally perpendicularly to the longitudinal axis L of the rod 86 (although, when rhomboidally shaped brackets are being produce, the cut will depart from the perpendicular by the angle, $\alpha$, as discussed above) and the two base concavities can be ground in a similar stepwise manner with a double-contoured diamond grinding wheel whose grinding edge is rounded or radiused to the appropriate degree so that the two concavities can be ground at the same time. FIGS. 24 and 25 show the saddles and both concavities already machined in the brackets 150 as the rod is cut into individual brackets.

Figure 22:
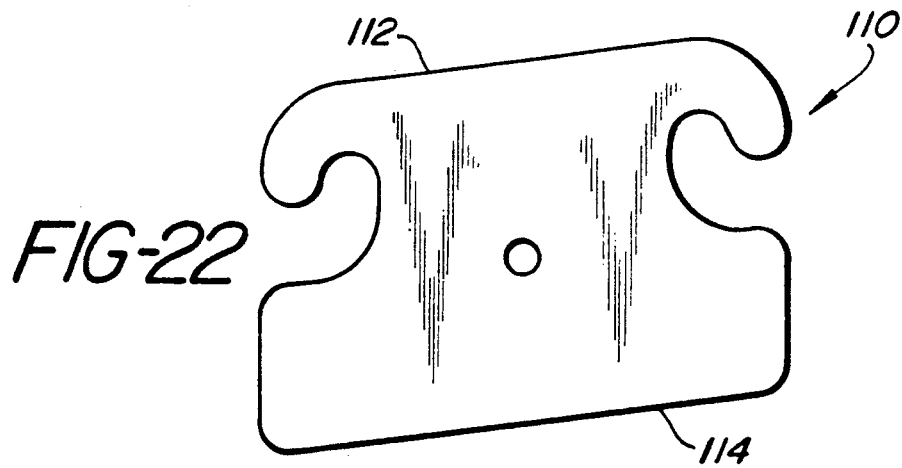
FIG. 22 is a view similar to FIG. 5, showing an alternative configuration to the top of the die.
Figure 20:
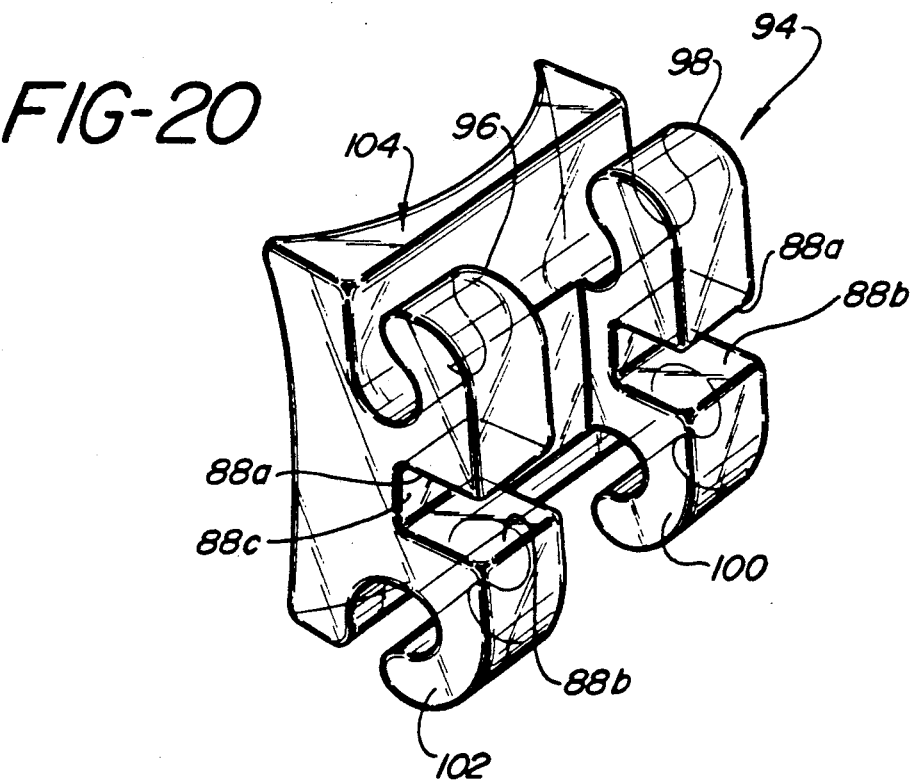
FIG. 20 is a perspective view of an orthodontic bracket machined from the blanks of FIGS. 17 and 18.
Figure 21:
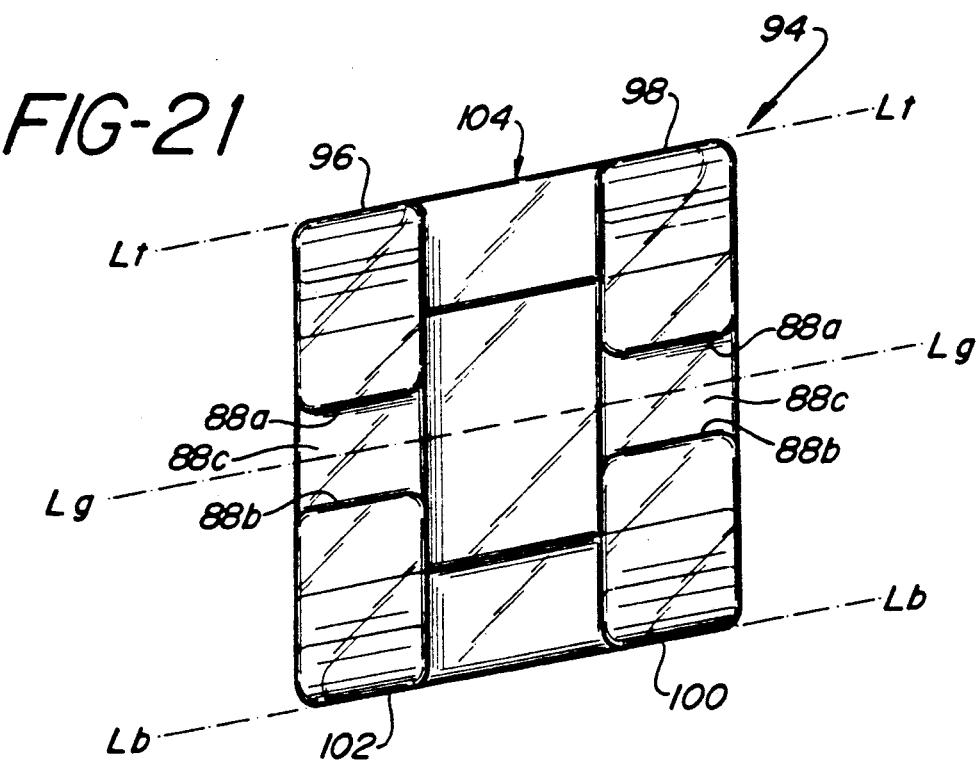
FIG. 21 is a front view of the bracket of FIG. 20.

FIGS. 20 and 21 are perspective and front views respectively of a bracket 94 made from the blank 92. As can be seen most clearly in FIG. 21, the brackets 94 produced in accordance with this alternative embodiment of the invention have rhomboidal configuration when viewed looking directly at the front of the bracket. Referring again to FIG. 21, both the body portion of the bracket (which includes the tie wings 96 98, 100, 102) and the base 104 have a rhomboidal configuration. preferably, the body portion and the base have the same rhomboidal configuration with the overall rhomboidal configuration of the body portion being superimposed on that of the base when the bracket is viewed looking directly at the front, as in FIG. 21. It is noted further that the archwire groove is oriented such that it is essentially parallel to the top and bottom surfaces of the bracket 94. That is the longitudinal axis Lg of the archwire groove is parallel to the lines Lt and Lb that are drawn through the top and bottom edges, respectively, of the bracket 94 when viewed looking at the front. To reduce the amount of grinding to a minimum, the rod may be grown such that the top and bottom faces are parallel to each other. This can be done using a die 110 configured as shown in FIG. 22, wherein the edge shown as 112 is parallel to the edge shown as 114. The rod (not shown) grown using this die 110 need only have the top and bottom surfaces lapped simultaneously. to insure uniform thickness, prior to the performance of the other machining operations, as described above.

After machining the brackets are preferably annealed under the conditions disclosed above for drawn rods. Then the brackets may be polished to smooth off contours and to remove any surface imperfections which could encourage propagation of cracks. If a polishing step is employed a flux polishing procedure would be recommended in which the flux is partially saturated with alumina so that the removal of alumina from the surface of the bracket will proceed at a controllable rate. One preferred flux is composed of 51.2 per cent $LiBO_2$, 12.8 per cent $Li_2B_4O_7$, 16 per cent $Al_2O_3$, and 20 per cent LiF (the percentages are by weight). The machined brackets are immersed in molten flux at 850° to 900° C. for a few minutes, e.g., from about four to about thirty minutes, and then removed. After cooling, the brackets can be immersed in aqueous hydrofluoric acid to remove any flux adhering to the surfaces of the brackets. Experience has demonstrated that the polishing step may be omitted and in fact it may be undesired in many cases because of the problems it causes in holding to the dimensional specifications. especially in the archwire grooves.

Other processes for polishing the surface of crystalline alpha-alumina objects are known, and may be used if desired. Such other processes are disclosed, for example, by Noble. in U.S. Pat. No. 4,339,300, and Manasevit. in U.S. Pat. No. 3,546,036.

In alternative embodiments of the invention, the most critical load bearing portions of the bracket are made of a crystalline alumina material, while the remainder is made of another transparent material, such as polycarbonate or polysulfone plastic, that is less expensive, easier to work, and easier to bond to the tooth. FIG. 10 shows one such alternative embodiment, wherein the bracket 44 is made predominately of transparent plastic 46 (e.g., polycarbonate) but wherein the archwire groove has crystalline alumina liners 48a 48b cemented herein. In another embodiment shown in FIG. 11, the bracket 50 has a transparent plastic base 52 (as the tooth contacting portion) cemented to a crystalline alumina body 54. In both of these alternative embodiments, the crystalline alumina portions can be made by a modification of the method described above, starting with a crystalline alumina rod of appropriate shape made by the EFG process.

Bonding a crystalline alumina bracket to the tooth (or to a plastic base to any other substrate) must be done with care. Many of the ordinary orthodontic cements (which are usually acrylic resins) will not adhere well to crystalline alumina without taking steps to enhance the adhesion. One means of enhancing the adhesion of a crystalline alumina bracket to the tooth is illustrated in FIGS. 13 and 14, in which a bracket 56 is shown that has an undercut or keyway 58 in the bottom or tooth-contacting surface of the bracket 56. Orthodontic cement filling the keyway 58 will have enhanced mechanical adhesion to the bracket 56 because of the undercut portion. This bracket 56 can be made by a method analogous to that described above, starting with the EFG process using a molybdenum die 60 having a top surface 28a shaped as shown in FIG. 12. The undercuts 58 can also serve as slots for the insertion of pliers or the like to facilitate removal of the brackets at the conclusion of the orthodontic treatment.

Figure 23:
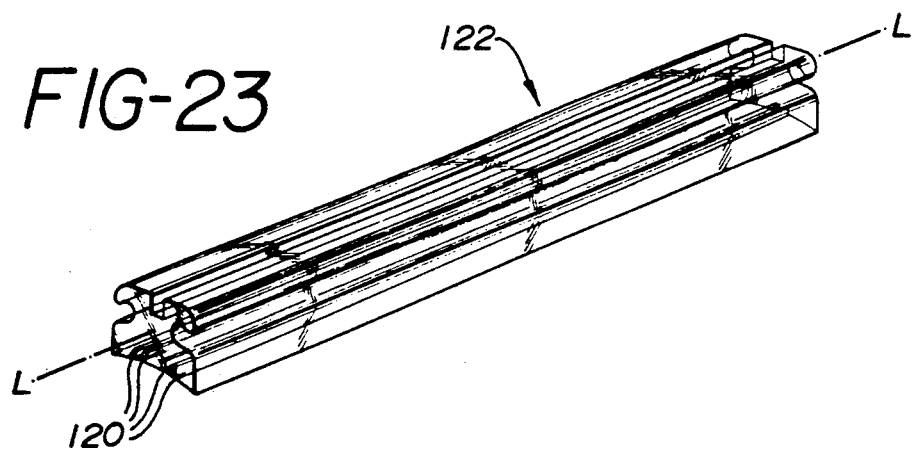
FIG. 23 is a view similar to FIG. 16, showing adhesion-promoting grooves machined in the bottom surface of the crystalline alpha-alumina rod.

An alternative means of enhancing the mechanical adhesion of the bracket to the surface of the tooth is shown in FIGS. 23-27. Small grooves 120 may be cut in the bottom surface of the rod 122. as is shown in FIG. 23. The grooves 120 extend the entire length of the rod 122. Typically, the grooves 120 will be from abcut 6 to 15 mils wide, with a depth about one and one-half times the width. The grooves 120 are preferably angled slightly (about 12°-15° from a direction that is generally perpendicular to the tooth contacting surface of the racket 150, as is seen most clearly in FIG. 27). The grooves 120 will extend in a direction that is generally parallel to the orientation of the archwire groove. That is, the grooves 120 will be generally parallel to the walls 88a, 88i b, 88c that define the archwire groove.

Figure 9:
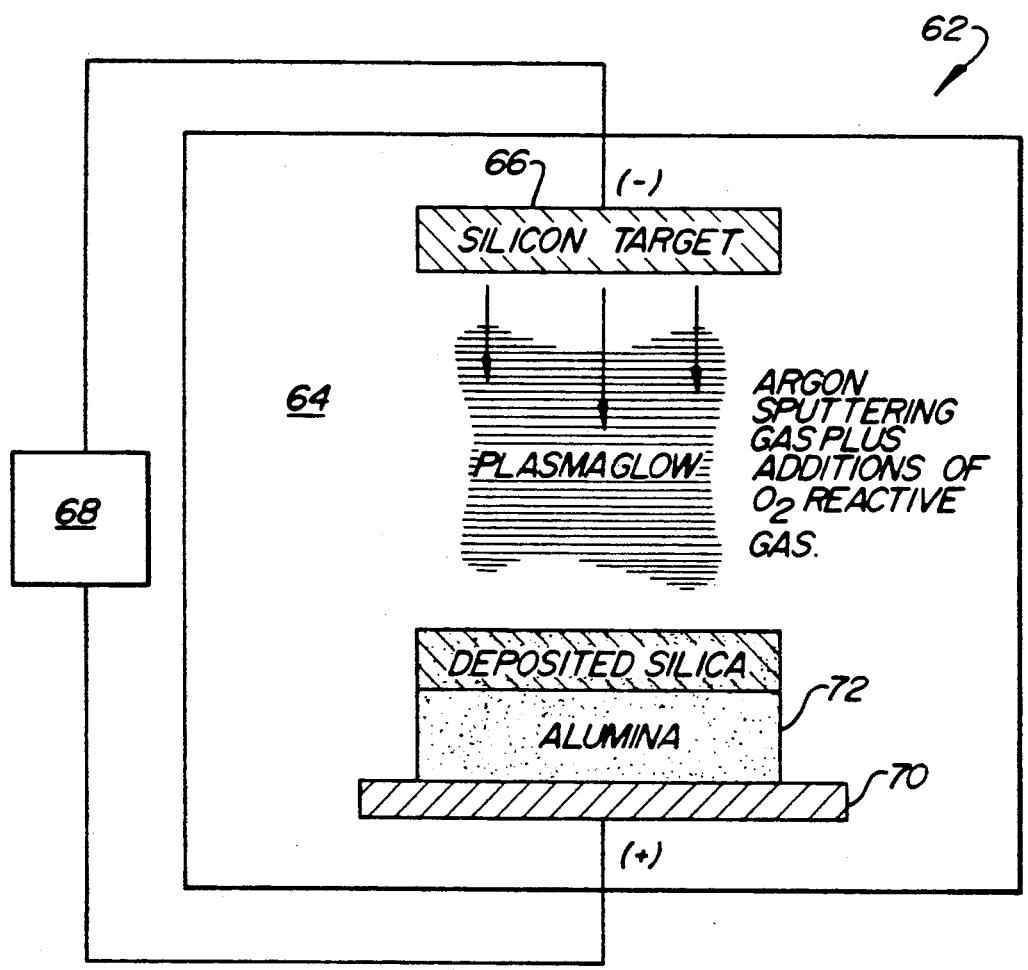
FIG. 9 is a schematic representation of apparatus for sputter coating silica on a crystalline alpha-alumina article.

Another means of enhancing the adhesion of cements such as acrylic resins to a crystalline alumina bracket is to alter the surface of the crystalline alumina in such a way as to increase the strength of the adhesive bond between the crystalline alumina and the cement. It is known, for instance, that a wide variety of silicone coupling agents can be used to enhance the adhesive force between siliceous substrates and a wide variety of thermosetting plastics. This technology may be utilized by coating the crystalline alumina surface that is to be in contact with the cement with a thin coating (usually thinner than about 10,000 angstroms, and preferably, up to about 1,000 angstroms) of a siliceous material such as silica, and then using silicone or silane coupling agents to enhance the bond of that surface to the cement in a manner analogous to that which is presently known. Examples of means for coating the crystalline alumina surface with a siliceous material are cathode sputtering, plasma deposition, and electron beam evaporation, all of which are known techniques, especially in the semiconductor arts. FIG. 9 is a schematic representation of apparatus suitable for sputter coating silica onto the surface of a crystalline alumina orthodontic bracket. The apparatus, shown generally as 62, includes a sputtering chamber 64 (which is vacuum tight) a target 66, in this case silicon metal, which is brought to cathode potential an RF or DC power supply 68 and a plate 70 for holding the cleaned and dried substrate 72 to be coated, in which the plate 70 is brought to anode potential A source of oxygen (not shown) introduoes oxygen into the chamber 64 so that the silicon metal 66 will be converted to silicon dioxide on the substrate 72. Reactive sputtering, such as is briefly outlined here, is known. For instance, see "The Basics of Sputtering" printed in December 1980 by Materials Research Corporation. Orangeburg N.Y. 10962.

The crystalline alumina bracket having its base or tooth-contacting surface sputter coated with silica or other siliceous material such as a glass has excellent affinity for silicone coupling agents such as A-174 (gamma-methacryloxypropyltrimethoxysilane). and by using such coupling agents the adhesion of the bracket to acrylic orthodontic cements is enhanced. Before applying the coupling agent, the silica-coated bracket should be heated in air for about 1 hour at 350° C. to convert the silica surface to a form that has a greater affinity for the coupling agent. For a fuller description of the use of a thin siliceous coating on the surface of crystalline alumina to enhance the adhesive bond to cements, see U.S. patent application Ser. No, 602,874, for "Crystalline Alumina Composites", filed on Apr. 23, 1984, and assigned to the same assignee as this application, now U.S. Pat. No. 4,595,598.

Another method for enhancing the affinity of the crystalline alpha-alumina bracket to silicone coupling agents is to heat the brackets to remove adsorbed water, and then treat the bracket with a dilute solution (e.g., a 2 to 2.5 weight per cent solution in toluene/propylene glycol monomethyl ether) of a silane coupling agent such as A-174. A heat treatment in air at 350° C. overnight (about 16 hours) has been found to be satisfactory. Alternatively, a short (about ½) hour) treatment in vacuum at 110° C. followed by heating in air at 350° C. for about three hours may be used. In both cases, the heat treated crystalline alumina bracket should be protected from moisture prior to the silane treatment. After treatment with the silane, a post-cure at, e.g., 110° C. for about 1 to 3 hours, is recommended to develop the optimum bonding strength.

Still another method of enhancing the affinity of the crystalline alpha-alumina bracket to silane coupling agents and/or acrylic adhesives is to first heat treat the brackets to remove adsorbed water, as described above. then coat them with a silane such as A-174, and heat the thus coated bracket to a temperature of about 650° C. to pyrolyze the silane and leave a coating that is essentially silica on the surface of the bracket. The bracket is then primed with a silane coupling agent such as A-174 in conventional manner.

The orthodontic brackets of the invention have enhanced esthetics because of the transparency of crystalline alumina. For instance, the transparency of crystalline alpha-alumina is such that a total of up to 98.5 per cent of light in the visible range is transmitted through it as determined by the integrating sphere method.

One of the stresses to which an orthodontic bracket will be subjected is torque, when an archwire of rectangular cross-section is employed to impart a torque force to the bracket. The strongest archwires in use today have a yield point of approximately 1000 gram-cenlimeters Therefore it is desirable that the orthodontic brackets of the invention be strong enough so that there is a high probability that they will survive a torquing force of 1000 gram-centimeters. To determine the probability of survival of the brackets of the invention when subjected to a torquing force a torque test is used and the results are subjected to Weibull statistical analysis. This type of statistical analysis is explained in "Mechanical Behavior of Ceramics", by R. W. Davidge pages 133 et seq., Cambridge Univ. press (1979). Briefly, the analytical procedure is the following:

The strength values for individual samples are arranged in ascending order. The nth ranked sample from a total of N samples has a probability of survival (of the strength value for the nth ranked sample) of $(n/(N+1)) \times 100$, in which n represents the ranking, with "1" being the rank of the weakest sample, and "N" being the total number of samples. The results may conveniently be presented in a graph of torque strength (x-axis) versus the probability of survival in per cent (y-axis).

Figure 28:
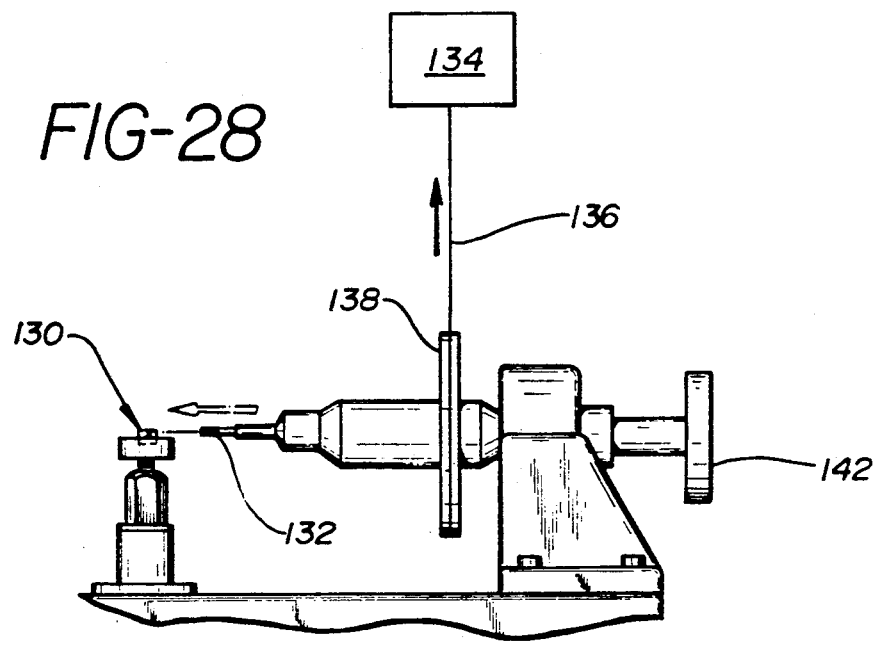
FIG. 28 is an enlarged view of the torque strength test set up.
Figure 29:
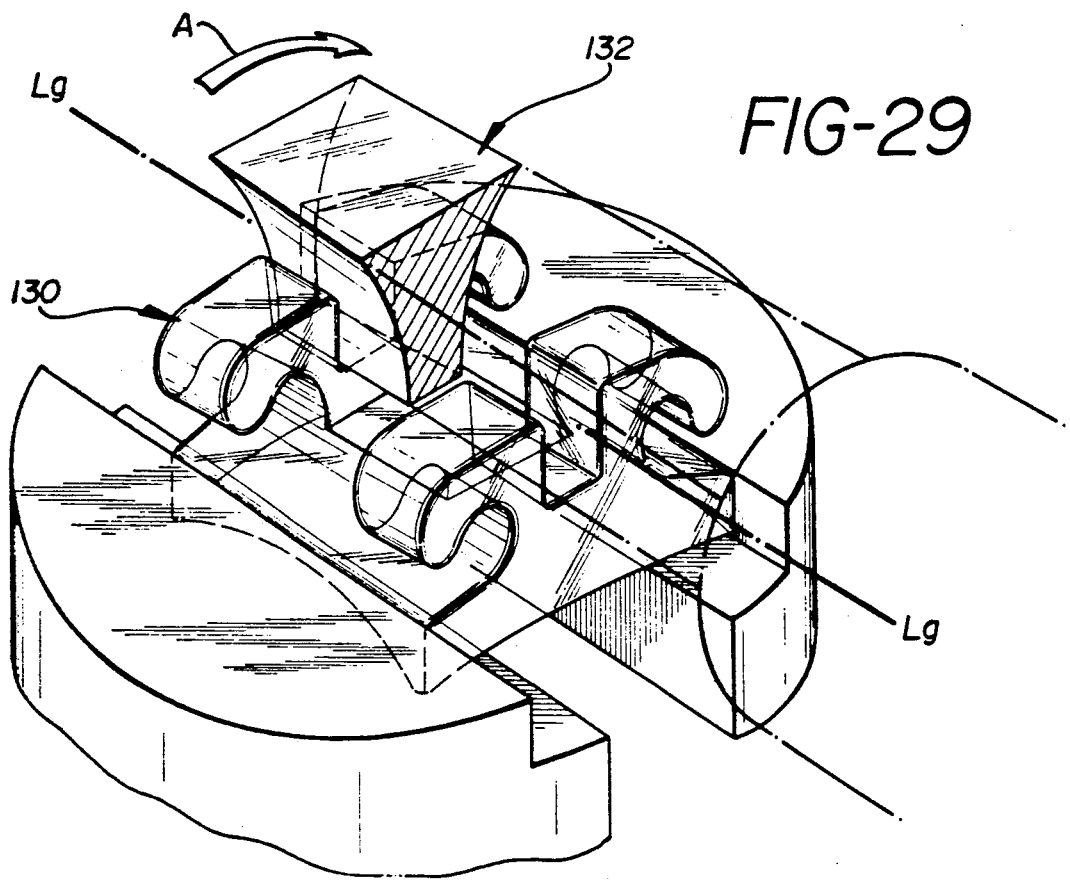
FIG. 29 is an enlarged perspective view of an orthodontic bracket mounted in the test set up, showing the movement of the test blade in the archwire slot.

The torque strength test set up is shown in FIGS. 28 and 29. The bracket 130 to be tested is fastened in the test stand with the slot facing upwards and with the longitudinal axis Lg of the archwire groove being aligned with the test blade 132. The test blade 132 is inserted in the archwire groove of the bracket 130 using a positioning wheel 141 to position the blade 132. The test blade 132 is sized to fit snugly in the archwire groove without exerting any expansion force on the side walls 88a, 88b (refer to FIGS. 20 and 26). The blade 132 is operatively connected to a load cell 134 via a wire 136 attached to a torque pulley 138. The load cell 134 is operatively connected to an Instron laboratory tensile tester (not shown). A rotational force is applied to the test blade 132 by the wire 136 acting on the torque pulley 138. Upon application of a force by the the wire 136, the test blade is twisted in the direction of the arrow A shown in FIG. 29. When testing alpha-alumina brackets, the test is continued until a tie wing fractures. When testing steel brackets the failure stress is where the tie wing first exhibits permanent deformation under the applied stress, prior to testing, the Instron is calibrated with a 2000 gram load cell using a 250-gram calibration weight. In applying the load, the torquing device (acting through the wire 136) moves at a rate of 2 centimeters per minute. (The torque pulley had a diameter of 7.62 centimeters.)

Figure 30:
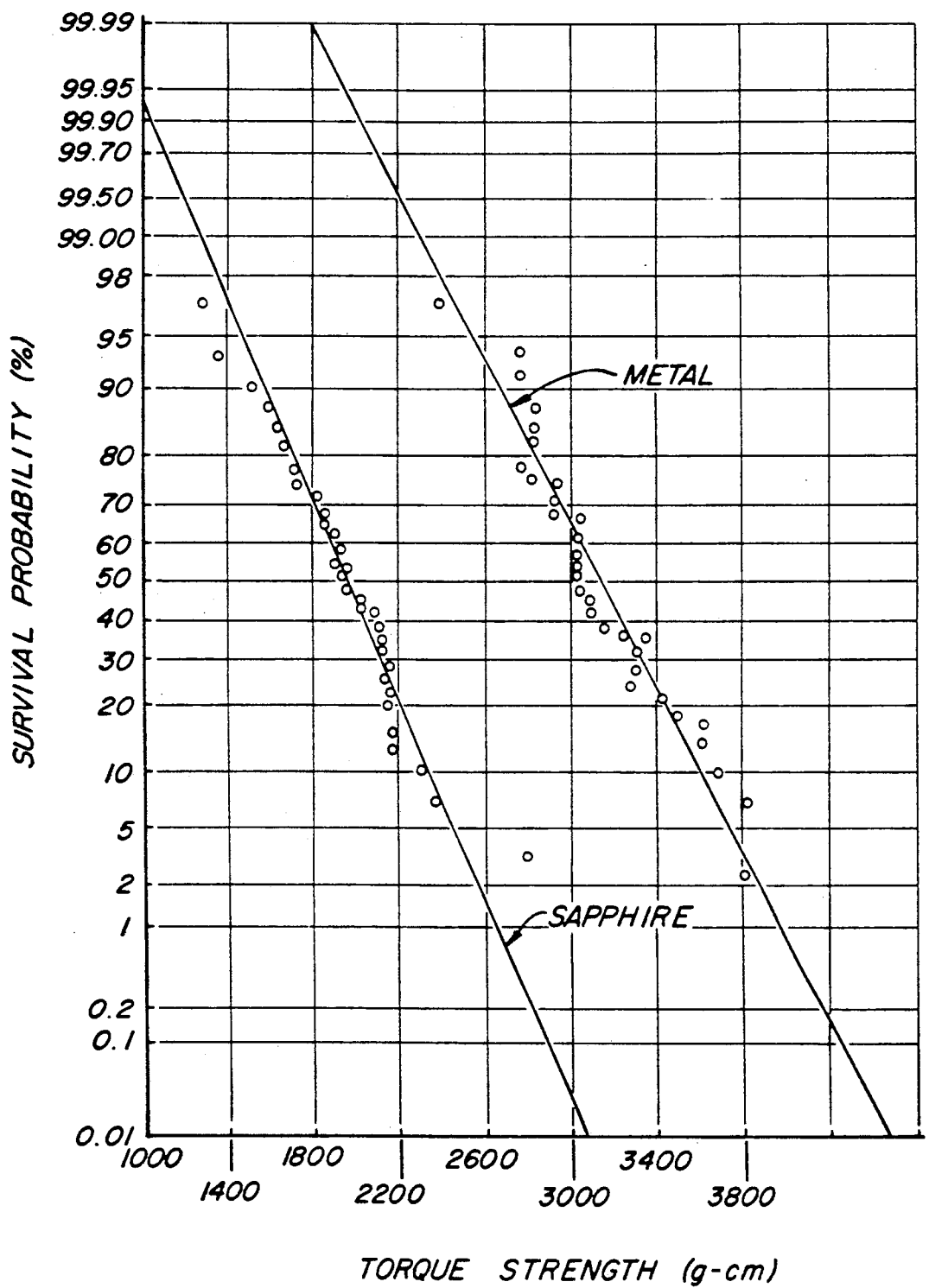
FIG. 30 is a graph of survival probability versus torque strength for metal and for the crystalline alumina orthodontic brackets of the invention.

The results of the torque strength testing are shown in FIG. 30 for brackets of the invention and for commercial stainless steel brackets. Thirty samples of each were tested. The crystalline alpha-alumina (sapphire) orthodontic brackets of the invention had torque strengths varying from 1257 gm-cm to 2800 gm-cm. and the stainless steel brackets had torque strengths varying from 2438 gm-cm to 3810 gm-cm. A brief summary of the results of the test is also displayed in Table I, which also summarizes the results of a similar Weibull statistical analysis of the torque strength of commercial polycrystalline alumina brackets made as described in the two Reynolds patents cited above.

TABLE I

| TORQUE STRENGTH - SURVIVAL PROBABILITY | | | |
|---|---|---|---|
| | 90% | 50% | 10% |
| Sapphire | 1600 | 1975 | 2375 |
| Stainless Steel | 2700 | 3150 | 3600 |
| Polycrystalline Alumina | 580 | 750 | 920 |

As the data presented above and displayed in the graph shown as FIG. 30 amply demonstrates, the crystalline alumina brackets of the invention have a probability of survival, using Weibull statistical analysis at a load on the archwire groove of 1000 gram-centimeters of torque, of greater than 98 per cent.

The invention has been described most particularly with respect to the use of crystalline alpha-alumina (sapphire) as the material from which the subject orthodontic brackets are made. However other crystalline alumina materials can be used in the invention. The limiting requirements are adequate strength (i.e., a 98 per cent probability of surviving a torquing stress of 1000 gram-centimeters on the archwire groove) and sufficient transparency so that the natural tooth color can be seen through the bracket. Other crystalline alumina materials that can be used include yttrium aluminum garnet, magnesium aluminum spinel, and alpha-alumina in which a small percentage of the aluminum atoms has been replaced with other elements to impart color and/or fluorescence to the crystal. For instance, fluorescence can be imparted to the crystal by the addition of small amounts (e.g. less than 1 mole per cent) of terbium oxide or cerium oxide to the aluminum oxide.

What is claimed is:

1. An orthodontic bracket comprising a base member for attaching to a tooth and a body member extending from the base member, said body member including walls defining an archwire groove, wherein said walls comprise crystalline alumina and wherein said bracket has a probability of survival of at least 98 per cent, by Weibull statistical analysis, when said walls are subjected to a torque force of 1000 gram-centimeters 2. The orthodontic bracket of claim 1 wherein said bracket is made entirely of crystalline alumina 3. The orthodontic bracket of claim 1 wherein said crystalline alumina is crystalline alpha-alumina.

4. The orthodontic bracket of claim 2 wherein said crystalline alumina is crystalline alpha-alumina.

5. The orthodontic bracket of claim 2 wherein said base member includes a surface intended for adhesive contact with a tooth wherein said surface includes an undercut portion for enhancing the mechanical adhesion of said surface to an orthodontic cement.

6. The orthodontic bracket of claim 2 wherein said base member includes a surface intended for adhesive contact with a tooth, wherein said surface includes at least one groove for enhancing the mechanical adhesion of said surface to an orthodontic cement 7. The orthodontic bracket of claim 6 wherein said one groove is oriented in a direction that is generally parallel to the walls that define the archwire groove.

* * * * *

UNITED STATES PATENT AND TRADEMARK OFFICE
CERTIFICATE OF CORRECTION

PATENT NO. : 5,066,225

DATED : November 19, 1991

INVENTOR(S) : Robin M. Forbes Jones, et al

It is certified that error appears in the above-identified patent and that said Letters Patent is hereby corrected as shown below:

Column 12, Claim 1, line 10, after "comprise", insert -- annealed --.

Signed and Sealed this

Fourteenth Day of September, 1993

Attest:

BRUCE LEHMAN

*Attesting Officer*      *Commissioner of Patents and Trademarks*